United States Patent [19]
Grossman et al.

[11] Patent Number: 4,776,350
[45] Date of Patent: Oct. 11, 1988

[54] EXTERNAL ELECTRODE FOR HEART STIMULATION AND CONNECTOR THEREFOR

[75] Inventors: Phillip A. Grossman, Woodinville; Harold L. Springer, Kirkland, both of Wash.

[73] Assignee: Physio-Control Corporation, Redmond, Wash.

[21] Appl. No.: 816,703

[22] Filed: Jan. 7, 1986

[51] Int. Cl.$^4$ .............................................. A61N 1/04
[52] U.S. Cl. .................................................... 128/799
[58] Field of Search ................ 128/419 PG, 631, 641, 128/640, 784, 783, 785, 798, 799

[56] References Cited

U.S. PATENT DOCUMENTS

| | | | |
|---|---|---|---|
| 3,295,515 | 1/1967 | Kahn | 128/640 |
| 3,518,984 | 7/1970 | Mason | 128/640 |
| 3,547,105 | 12/1970 | Ramme | 128/640 |
| 3,599,629 | 8/1971 | Gordy | 128/640 |
| 3,606,881 | 9/1987 | Weedson | 128/641 |
| 3,721,246 | 3/1973 | Landis | 128/783 |
| 3,993,049 | 11/1976 | Kater | 128/640 |
| 4,109,648 | 8/1978 | Larke et al. | 128/639 |
| 4,166,453 | 9/1979 | McClelland | 128/639 |
| 4,262,982 | 4/1981 | Kenny | 128/419 P |
| 4,273,135 | 6/1981 | Larimore et al. | 128/640 |
| 4,274,420 | 6/1981 | Hymes | 128/798 |
| 4,300,575 | 11/1981 | Wilson | 128/798 |
| 4,317,278 | 3/1982 | Carmon et al. | 29/878 |
| 4,319,579 | 3/1982 | Cartmell | 128/640 |
| 4,349,030 | 9/1982 | Belgard et al. | 128/419 PG |
| 4,370,984 | 2/1983 | Cartmell | 128/640 |
| 4,419,998 | 12/1983 | Heath | 128/639 |
| 4,423,732 | 1/1984 | Tarjan et al. | 128/419 P |

Primary Examiner—William E. Kamm
Attorney, Agent, or Firm—Christensen, O'Connor, Johnson & Kindness

[57] ABSTRACT

An electrode (10) adapted for external heart stimulation, and a connector (52) therefor. The electrode includes a first conductive member (14) having a sheet-like configuration and an area resistivity of at least 0.003 ohm-cm$^2$, and a second conductive member (16) having a sheet-like configuration, and having one surface in contact with the first conductive member and a second surface adapted to engage the patient's skin. Current is introduced at a centrally located portion of the first conductive member. The second conductive member has an area resistivity greater than the area resistivity of the first conductive member, such that the first conductive member acts as a distributor to distribute current density over the area of the electrode. The connector apparatus includes a conductive post (30) from the electrode, a connector having a body shape to form a socket (56), an opening through which the post can extend into the socket, a plurality of outwardly projecting rings encircling the opening, and adhesive means (48) for adhesively connecting the rings to the surface of the electrode adjacent the post.

12 Claims, 5 Drawing Sheets

EXTERNAL ELECTRODE FOR HEART STIMULATION AND CONNECTOR THEREFOR

FIELD OF THE INVENTION

The present invention relates to external electrodes for use with a heart stimulating device such as a pacemaker or a defibrillator. Such electrodes are applied to the skin of a patient, and used to stimulate the patient's heart muscles via an electrical impulse delivered to the patient through the electrodes. The present invention also relates to connectors for establishing electrical connection between such an electrode and a conductive line connected to the heart stimulating device.

BACKGROUND OF THE INVENTION

A pacemaker is a therapeutic physiological instrument that is adapted for connection to a patient through pacing electrodes. The pacemaker operates by providing a periodic electrical stimulus to the patient through the electrodes in order to maintain the patient's heartbeat. In the past, pacemakers have generally been internal (e.g., implantable), wherein the pacemaker electrodes are connected directly to the patient's heart. Prior external pacemakers have seen limited use, almost exclusively with unconscious patients, because of the pain associated with the delivery of a pacing stimulus through a patient's skin. It has not been uncommon for external pacing electrodes to produce crescent-shaped burns on a patient's skin adjacent the electrode edge when the electrodes were used over an extended period of time or with a high pacing current. There has therefore been a long-felt need for an improved electrode for external pacing that was suitable for use with a conscious patient and over an extended period of time.

To the extent that external pacing electrodes have been used in the past, they have generally been permanently attached to cables that are in turn attached to the pacemaker. To increase the versatility and usefulness of external pacing electrodes, it would be desirable to provide a disposable electrode having a small conductive terminal permanently affixed to the electrode, and to provide a connector whereby one end of the cable could be electrically connected to the terminal when pacing was required. Prior pacing electrodes have tended to avoid this approach, however, because of the difficulty in providing a connector that was easy to connect and disconnect but that was also sufficiently moisture proof for external pacing use.

A defibrillator is a therapeutic physiological instrument that is used to deliver an electric shock to a patient who is experiencing a cardiac arrythmia such as ventricular fibrillation. Such an electric shock frequently terminates the chaotic activity characteristic of an arrythmia, and restores the normal pumping action of the heart. Unlike pacemakers, many prior defibrillators have been designed for external use, wherein the electric shock is delivered to the patient via electrodes that contact the patient's skin through a layer of conductive gel or the like. The pain and burn factors associated with external pacemakers have generally not been a factor in limiting the use of external defibrillators, because defibrillation is only used for unconscious patients, because the use is intermittent rather than continuous, and because of the life-threatening nature of a cardiac arrythmia. Nevertheless, it would be an advantage to provide an improved defibrillator electrode in which the tendency to produce burns was not present.

SUMMARY OF THE INVENTION

The present invention provides an electrode adapted for external use to stimulate a patient's heart, as well as a connector for connecting such an electrode to a cable leading to the heart stimulating equipment. The electrode of the present invention reduces the current density concentrations around the electrode edge characteristic of prior external electrodes for heart stimulation.

In one aspect, the present invention provides an electrode adapted for connection to a patient's skin to provide electrical current to the patient to stimulate the patient's heart. The electrode comprises a first conductive member having a sheet-like configuration and an area resistivity of at least 0.003 ohm-cm$^2$. Means are provided for introducing electrical current to a centrally located portion of the first conductive member. The electrode further comprises a second conductive member having a sheet-like configuration, and having one surface in contact with the first conductive member and a second surface adapted to engage the patient's skin. The second conductive member has an area resistivity greater than the area resistivity of the first conductive member. Because of the higher area resistivity of the second conductive member, the first conductive member acts as a distributor to distribute the current density more evenly over the surface of the electrode. However, the comparatively high resistivity of the first conductive member, as compared to metal, reduces the tendency of the current density to concentrate at the electrode edge.

In another aspect, the present invention provides an apparatus for connecting a pacing electrode to a conductor. The apparatus comprises a conductive post extending outward from the electrode and electrically connected to patient engaging conductive means in the electrode. The apparatus further includes a connector comprising a body shaped to form a socket, the body having an opening on one side through which the post can extend into the socket, and a plurality of outwardly projecting rings encircling the opening. Contact means are provided within the socket for making electrical connection with the post. Adhesive means connect the rings to the surface of the electrode adjacent the post when the post extends into the socket.

DETAILED DESCRIPTION

Figure 1:
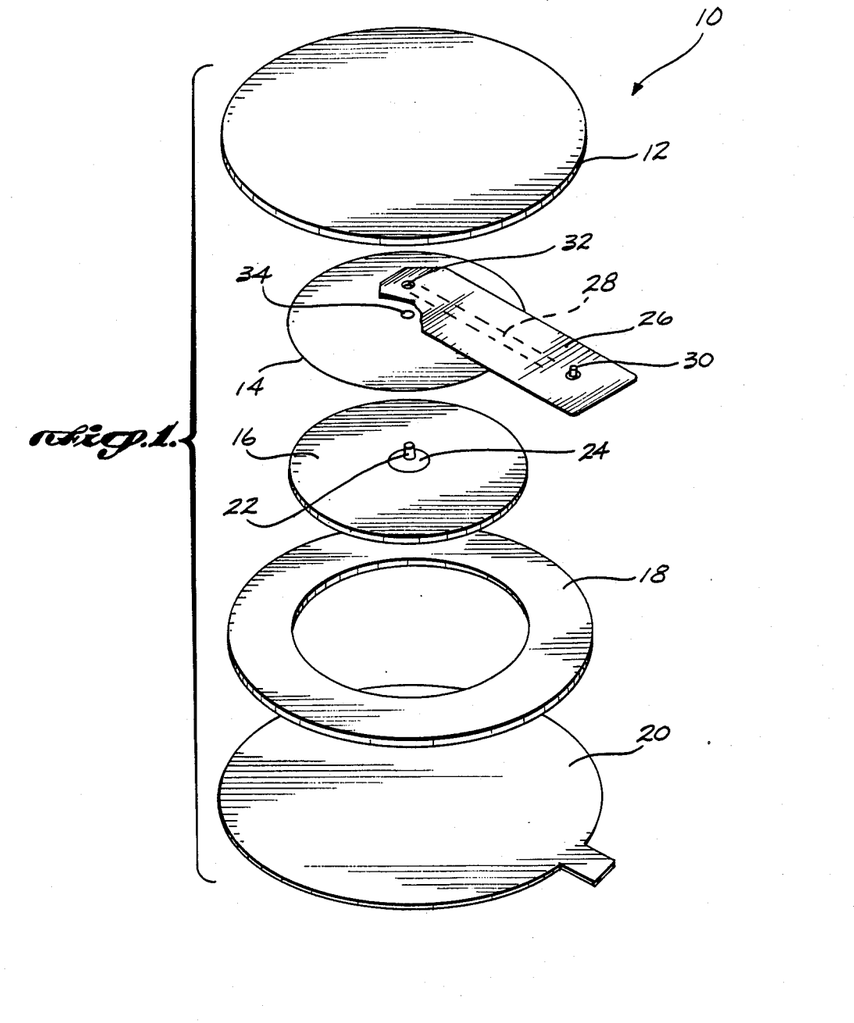
FIG. 1 is an exploded perspective view of a heart stimulating electrode according to the present invention.

One preferred embodiment of the electrode of the present invention is illustrated by electrode 10 of FIG. 1. Electrode 10 is particularly adapted for pacing use, and has a generally circular shape and comprises cover 12, first conductor 14, second conductor 16, ring 18, release liner 20 and tab 26. Cover 12 and ring 18 are fabricated from a non-conductive, medical grade, closed cell foam material such as cross-linked polyethylene. Cover 12 includes a pressure sensitive adhesive on its lower surface, and ring 18 includes a pressure sensitive adhesive on its upper surface and a hypoallergenic pressure sensitive adhesive on its lower surface. When the electrode is assembled, the upper surface of ring 18 is joined to the outer edge of cover 12, to form a circular cavity in which first conductor 14 and second conductor 16 are positioned, with the lower surface of the second conductor flush and continuous with the lower surface of ring 18, and with the upper surface of second conductor 16 in contact with the lower surface of first conductor 14. As described below, the lower surface of second conductor 16 includes a conductive adhesive layer. The entire patient engaging surface of electrode 10 is therefore adhesively surfaced. Prior to use, the patient engaging surface is protected by release liner 20 that may comprise siliconized high density polyethylene.

Tab 26 extends radially from the center of the electrode between first conductor 14 and cover 12, and includes embedded electrically conducting strip 28 that is in electrical contact with conductive post 30 at the outer end of tab 26. The inward end of tab 26 includes opening 32 that passes through strip 28. When the electrode is assembled, metallic eyelet 22 extends through an opening 34 in the center of first conductor 14 and through opening 32 in tab 26. The eyelet is fastened to first conductor 14 by crimping. Insulating disk 24 is positioned between the first and second conductors, and serves to insulate the second conductor from eyelet 22. The insulating disk is composed of a nonconducting vinyl that may be coated with a pressure sensitive adhesive to facilitate assembly of the electrode. The diameter of openings 32 and 34 are adjusted relative to the diameter of eyelet 22 such that the eyelet establishes electrical connection between strip 28 and first conductor 14 when the electrode is assembled and the eyelet crimped.

First conductor 14 is composed of a conductive polymer such as a carbon-filled vinyl or carbon filled rubber material. The area resistivity of first conductor 14 is on the order of 0.003 ohm-cm$^2$ or higher, the particular value of area resistivity depending upon the application to which the electrode is to be put. For example, for the high current densities used in defibrillation, an area resistivity on the order of 0.003 ohm-cm$^2$ would be suitable. On the other hand, in the electrode illustrated in FIG. 1 that is particularly adapted for pacing, a preferred area resistivity would be 0.25 ohm-cm$^2$ or higher, with a most preferred value being about 2.7 ohm-cm$^2$. By way of example, an area resistivity of 2.7 ohm-cm$^2$ for first conductor 14 could be achieved by using a conductive polymer having a volume resistivity of 35 ohm-cm, and by making the thickness of first conductor 14 equal to 0.76 mm, the area resistivity being the volume resistivity times the thickness of the first conductor. In general, the exact resistivity of the first conductor will be selected based on a number of factors, such as the pacing therapy, the nature of the conductive gel used at the electrode/skin interface, and other factors that will be clear to those skilled in the art.

Second conductor 16 is composed of a conductive material that may be identical to the conductive polymer used for the first conductor. However, in accordance with the present invention, the area resistivity of the second conductor is greater than the area resistivity of the first conductor. In a preferred embodiment, the area resistivity of the second conductor is at least ten times greater than the area resistivity of the first conductor, and most preferably about 500–1,500 times greater than the area resistivity of the first conductor. It has been found that by providing such a ratio between the area resistivities of the first and second conductors, high current densities do not occur around the edges of the electrode, and an essentially uniform current distribution is maintained over the area of the electrode.

In a preferred arrangement, second conductor 16 comprises a laminate composed of an electrically conductive rubber sheet, sandwiched between two layers of conductive gum adhesive. A suitable material for the conductive gum adhesive layers is a natural gum (e.g., Karaya) based material loaded with graphite or an ionic substance. In this preferred embodiment, the area resistivity of the rubber layer is higher than the area resistivity of each gum adhesive layer. The purpose of the laminate structure is to provide an adhesively-surfaced second conductor that is not prone to the development of hot spots or areas of high current density. In particular, for many commerciallyavailable conductive gum adhesives, there is a tendency for the conductive adhesive layer to be poorly mixed, such that there are globules of unmixed gum adhesive in certain portions of the material and concentrations of conductive substances in other parts of the material. The result of such a structure is that the current tends to flow preferentially through the areas where the conductor is concentrated. Therefore, by incorporating the layer of conductive rubber between the layers of conductive gum adhesive, the tendency to produce hot spots is reduced. This is particularly true in the preferred embodiment, wherein the resistivity of the rubber layer is greater than the resistivity of the gum adhesive layers.

In a pacing electrode embodiment in which first conductor 14 has an area resistivity of 2.7 ohm-cm$^2$, second conductor 16 would be constructed such that it had a composite or total area resistivity greater, and preferably about 1,000 times greater, than the area resistivity of the first conductor. By way of example, second conductor 16 could be constructed such that the gum adhesive layers each had volume resistivities of 7,500 ohm-cm and thicknesses of 0.89 mm, and the rubber layer could be constructed from a material having a volume resistivity of 25,000 ohm-cm, and a thickness of 0.51 mm. These values would provide area resistivities for the gum adhesive layers of 667 ohm-cm$^2$, and an area resistivity of the rubber layer of 1,275 ohm-cm$^2$, to provide a total area resistivity for the second conductor of 2,609 ohm-cm$^2$.

Because first conductor 14 has a lower area resistivity than second conductor 16, electrical current provided to the center of the first conductor adjacent opening 32 has a tendency to spread out laterally through the first conductor before flowing downward through the second conductor into the patient. The resistance of the first conductor, however, limits the amount of current flowing through the outer circumference of the first conductor relative to the current flowing near the center of the first conductor, i.e., current flowing out of the electrode near the electrode edge must travel a comparatively longer path through the resistive first conductor. The tendency of the pacing electrode to cause crescent-shaped burns at the electrode circumference is thereby significantly reduced, and the pacing electrode of the present invention can be used with a conscious patient without undue discomfort. The same considerations apply to defibrillator electrodes constructed in accordance with the principles of the present invention.

Figure 2:
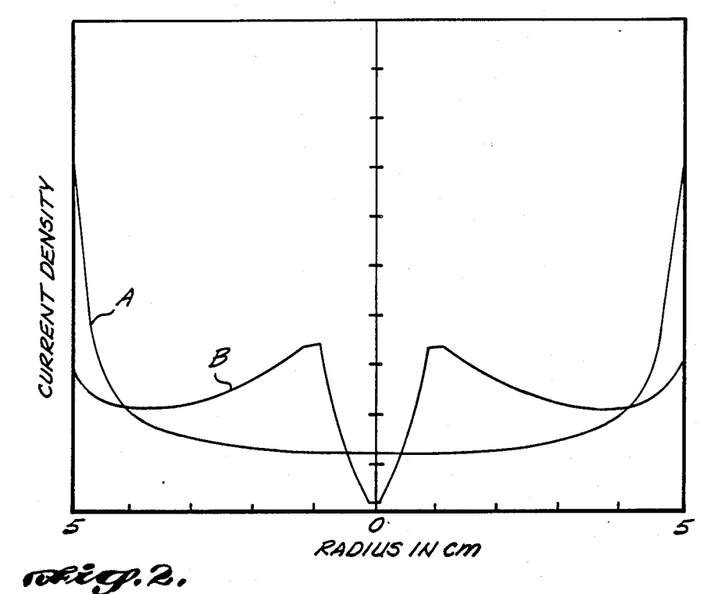
FIGS. 2-5 are graphs showing current density profiles for electrodes according to the present invention and for a metal electrode.

FIGS. 2–5 present a more quantitative picture of the improved current flow characteristics provided by the electrode of the present invention. The graphs of FIGS. 2–5 were produced by a computer using a conventional, two-dimensional finite element analysis program. Referring initially to FIG. 2, curve A shows the current density as a function of radius for a circular metal electrode having a radius of 5 cm. Curve A clearly demonstrates the tendency of the current density to rise steeply near the edges of the electrode, and it is this feature of metallic electrodes that tends to produce the crescent-shaped burns in patients receiving external pacing therapy. Curve B of FIG. 2 shows the current density as a function of radius for a pacing electrode constructed in accordance with the principles of the present invention. The electrode corresponding to curve B has a first conductor 14 that has a volume resistivity of 35 ohm-cm and a thickness of 0.76 mm, to produce an area resistivity of 2.7 ohm-cm$^2$. Second conductor 16 has a three-layered structure in which each of the outer layers has a volume resistivity of 7,500 ohm-cm and a thickness of 0.89 mm, to produce an area resistivity of 667 ohm-cm$^2$. The inner layer of second conductor 16 has a volume resistivity of 25,000 ohm-cm and a thickness of 0.51 mm, to produce an area resistivity of 1,275 ohm-cm$^2$. Thus the total area resistivity of second conductor 16 was 2,610 ohm-cm$^2$, approximately 1,000 times greater than the area resistivity of first conductor 14. Finally, the electrode corresponding to curve B had an insulating disk 24 having a radius of 1 cm. As described above, insulating disk 24 prevents current from flowing directly into the center portion of second conductor 16. As illustrated in FIG. 2, the current density for the above-described electrode (curve B) rises from a very low value at the center of the electrode to a peak at a radius approximately equal to 1 cm, then gradually decreases until near the outer edge of the electrode, whereupon a small increase in current density occurs. The dip in current density near the electrode center is due to insulating disk 24. Comparison of curves A and B in FIG. 2 clearly reveals the dramatic decrease in current density at the edge of the electrode that is achieved by use of the electrode of the present invention.

Figure 3:
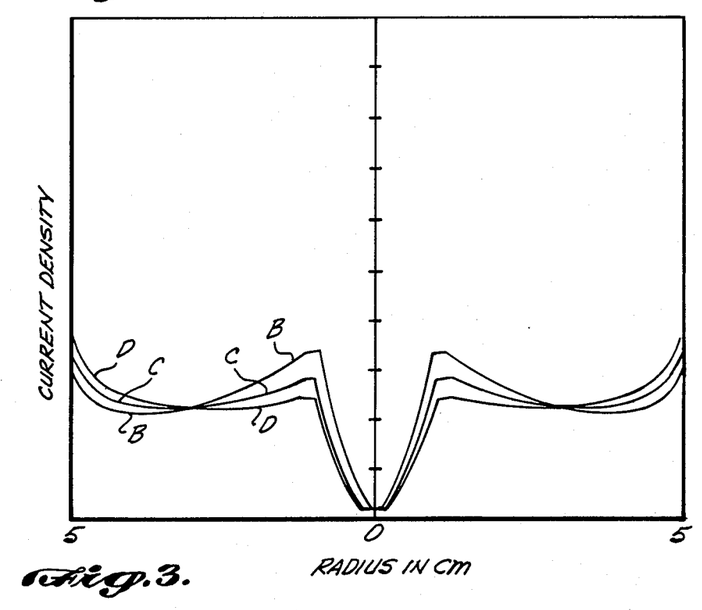

FIG. 3 illustrates the variation in the current density profile as the parameters of first conductor 14 are varied. Curve B in FIG. 3 corresponds to curve B in FIG. 2. Curve C in FIG. 3 illustrates the effect of increasing the thickness of first conductor 14 from 0.76 mm to 1.67 mm. As illustrated, the current density near the edge of the insulated disk decreases, while the current density near the electrode edge increases somewhat. As described above, first conductor 14 acts as a distributor to spread the current out over the area of the electrode. For this reason, the effective resistance, as opposed to the area resistance, of first conductor 14 is equal to the volume resistivity divided by $\pi$ times the thickness of the first conductor. Thus, as the thickness of the first conductor increases, the effective resistance decreases, leading to an increased current density at the electrode edge. Further increases in the thickness of first conductor 14 would cause the current density at the electrode edge to continue to increase, eventually yielding an electrode in which the current distribution was not a significant improvement over the metal electrode shown in curve A in FIG. 2. Curve D of FIG. 3 illustrates the effect of decreasing the volume resistivity of the first conductor by a factor of 10 from 35 ohm-cm to 3.5 ohm-cm. This change has an effect similar to that of increasing the thickness, i.e., the change leads to a reduction of current density around the edges of insulating disk 24, and to an increase in current density near the electrode edge.

Figure 4:
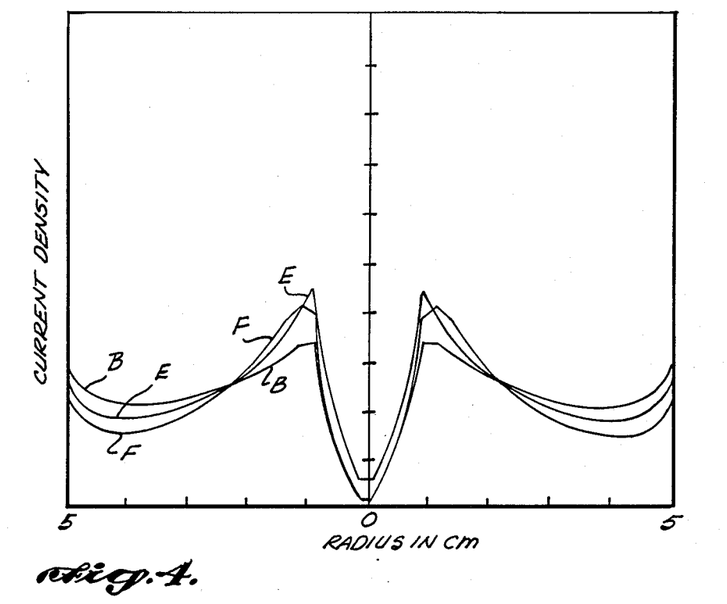

FIG. 4 illustrates the effect of decreasing the area resistivity of second conductor 16. Curve B in FIG. 4 is identical to curve B in FIGS. 1 and 2. Curve E in FIG. 4 shows the current density profile for an electrode similar to the electrode of curve B, except that the thickness of each of the layers of second conductor 16 has been reduced by 50 percent. As illustrated, this change produces an improved (i.e., reduced) current density at the electrode edge, but at the expense of a higher current density near the edge of the insulating disk. Curve F in FIG. 4 shows the effect of decreasing the volume resistivity of each of the layers of the second conductor by a factor of 10. The result is a generally similar change in which the current density at the electrode edge decreases while the current density at the edge of the insulating disk increases.

Figure 5:
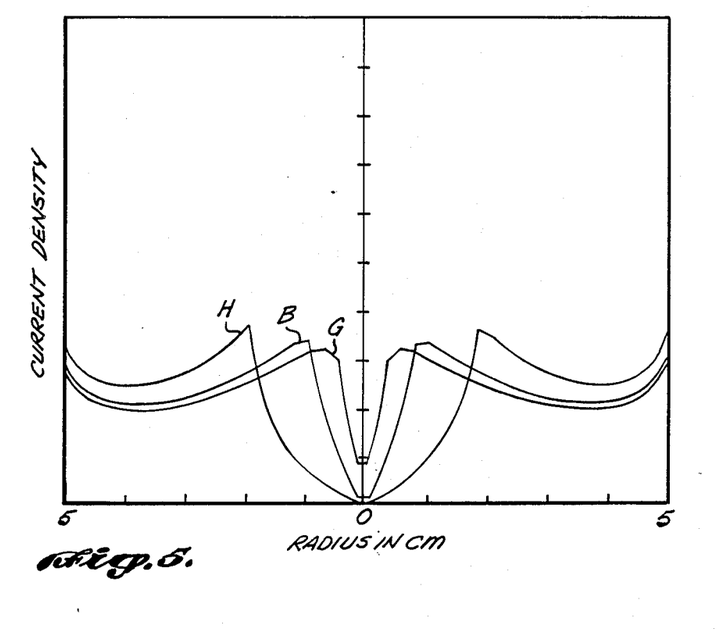

FIG. 5 illustrates the effect of varying the radius of insulating disk 24. Curve B in FIG. 5 is identical to curve B in FIGS. 2–4. Curve H in FIG. 5 shows the current density profile for an electrode having an insulating disk with a radius of 2 cm, while curve G of FIG. 5 shows the current density profile for an electrode in which the insulating disk has a radius of 0.5 cm. It is apparent from FIG. 5 that increasing the radius of the insulating disk increases the current density at the insulating disk edge, as well as at the electrode edge. In effect, increasing the radius of the insulating disk causes a given amount of current to flow through a smaller area, thereby leading to increased current densities. It is therefore apparent that the radius of the insulating disk is preferably kept small, in the range of 0.5–1 cm.

Figure 6:
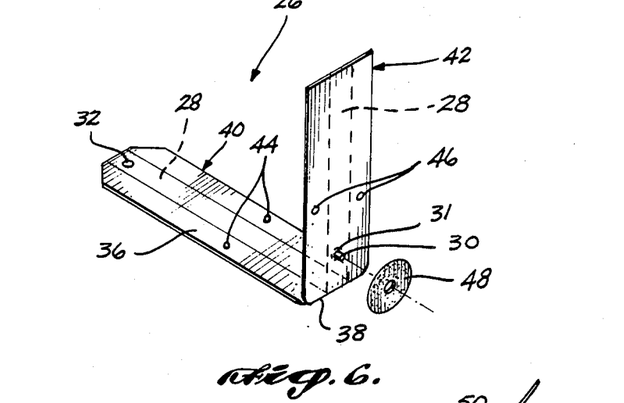
FIG. 6 is an exploded, perspective view of the tab.
Figure 7:
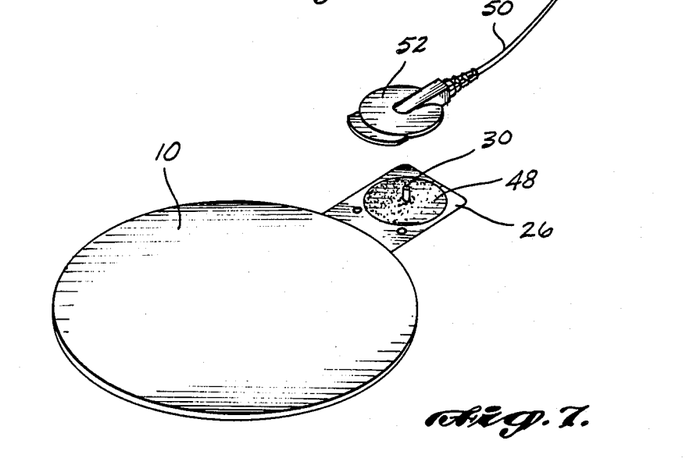
FIG. 7 is a perspective view of a pacing electrode and a connector according to the present invention.

The construction of tab 26 is illustrated in greater detail in FIG. 6. Tab 26 comprises an elongated plastic element 36 having conductive strip 28 deposited on one surface thereof. Strip 28 is contiguous at one end with opening 32 that receives eyelet 22, as described in relation to FIG. 1. Post 30 extends through a second opening 31 in element 36, opening 31 also being contiguous with strip 28. The tab is assembled by folding element 36 along line 38 near the midpoint of the element, thereby dividing the element into lower section 40 and upper section 42. Line 38 is positioned such that upper section 42 is slightly shorter than lower section 40, such that when the upper section is folded over the lower section, upper section 42 does not block opening 32. The folded together upper and lower sections are secured to one another by means of a suitable adhesive. Post 30 includes an enlarged diameter lower section (shown in phantom in FIG. 6) that is held between the folded together upper and lower sections, thereby securing post 30 in tab 26. Openings 44 are positioned to either side of strip 28 in lower section 40, and corresponding openings 46 are positioned at either side of strip 28 in upper section 42. When the upper and lower sections are folded together and joined, openings 44 are contiguous with openings 46, to create openings that pass entirely through tab 26. The tab shown in FIG. 6 includes adhesive disk 48 applied to the surface of the tab surrounding post 30, the purpose of adhesive disk 48 also being described below.

Figure 8:
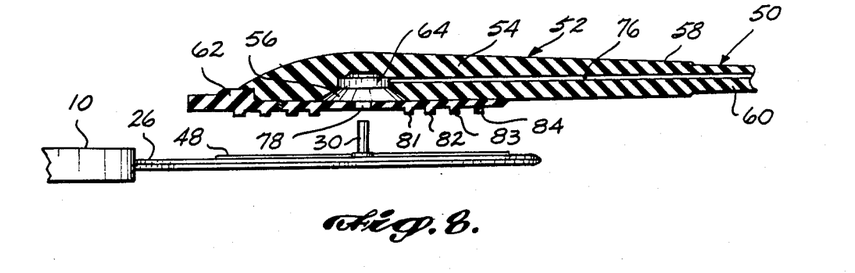
FIG. 8 is a partial cross section view of the connector.
Figure 9:
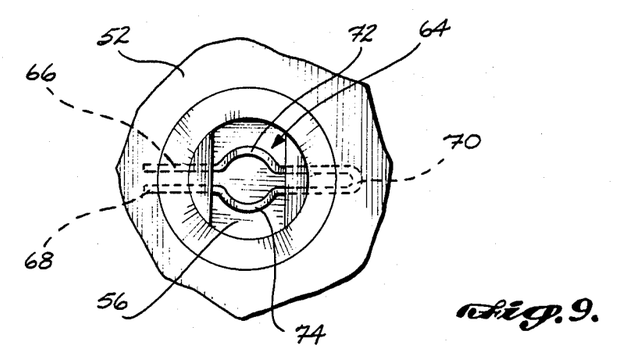
FIG. 9 is a bottom plan view of the electrical contact.

FIGS. 7–11 illustrate the means by which pacing electrode 10 may be attached to cable 50 that in turn may be attached to a cardiac pacemaker. The attachment between electrode 10 and cable 50 is effected by means of connector 52 that comprises body 54 that is shaped so as to form the top and sidewalls of socket 56. The body includes strain relief 58 that serves to connect the body to insulating sheath 60 of cable 50. Cover 62 covers the bottom portion of body 54 and also forms the bottom wall of socket 56. Body 54 may be composed of a comparative hard insulating material such as plastic, and cover 62 may be composed of a comparatively soft insulating material such as soft vinyl rubber. Electrical contact 64 is mounted in the upper portion of socket 56 by body 54, such that the contact extends laterally along a diameter of the socket. As illustrated in FIG. 9, contact 64 comprises side portions 66 and 68 interconnected by U-shaped portion 70. Side portions 66 and 68 include arcuate portions 72 and 74 respectively, the arcuate portions extending away from one another such that together they form a portion of a circular band for receiving and making electrical contact with post 30, as described more fully below. Contact 64 is electrically connected to conductive line 76 extending through strain relief 58 from cable 50.

Figure 10:
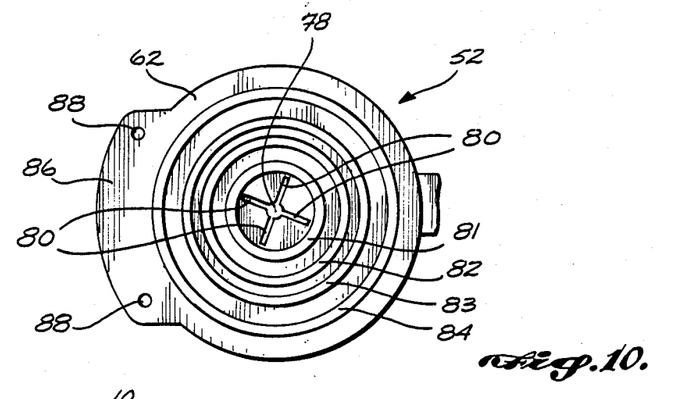
FIG. 10 is a bottom plan view of the connector.
Figure 11:
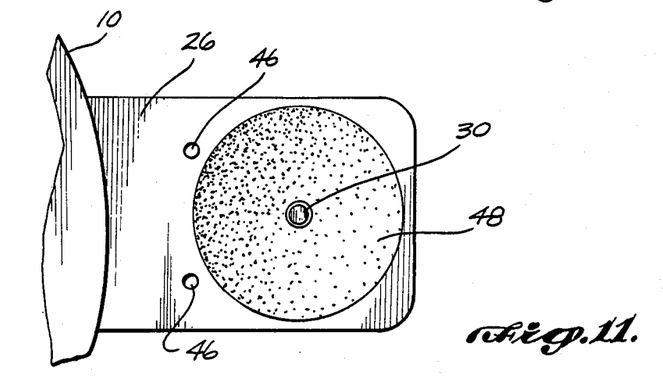
FIG. 11 is a top plan view of the tab.

As best shown in FIGS. 8 and 10, cover 62 includes central opening 78 and radial slits 80 extending outwardly from opening 78. The lower surface of cover 62 also includes outwardly projecting rings 81–84 encircling opening 78 and slits 80, and lip 86 having circular projections 88 formed therein. Opening 78 is positioned such that when cover 62 is secured to body 54, opening 78 is symmetrically and centrally positioned with respect to socket 56 and with respect to arcuate portions 72 and 74 of contact 64. The opening preferably has a diameter slightly smaller than the diameter of post 30. However, because cover 62 is composed of a soft rubber material, the post can be inserted through opening 78, the flexure of the cover necessary to accommodate the post being provided by slits 80. Ring 81 completely surrounds opening 78 and slits 80. In a similar manner, ring 82 surrounds ring 81, ring 83 surrounds ring 82, and ring 84 surrounds 83.

Connection between connector 52 and electrode 10 is accomplished in the manner indicated in FIG. 8. The connector is positioned over post 30 such that the post is aligned with opening 78 in cover 62 and with arcuate portions 72 and 74 of contact 64. The connector is then pushed downward until post 30 extends through opening 78 into socket 56 and is engaged by arcuate portions 72 and 74, contact 64 thereby making electrical contact with the post and establishing an electrical path between the connector and the patient engaging lower surface of secondary conductor 16 of electrode 10. Contact 64 is in turn electrically connected through line 76 to the conductor of cable 50 for completing the electrical connection between the patient and the pacemaker to which cable 50 is connected. When connector 52 is fully inserted onto post 30, rings 81–84 make contact with adhesive ring 48 on tab 26, thereby sealing cover 62 to tab 26. Each ring 81–84 therefore creates a seal that prevents fluids from leaking between the connector and the tab. The provision of four rings 81–84 makes the seal virtually immune to failure, inasmuch as the separation between the rings and the pliable nature of cover 62 renders it unlikely that all four rings would simultaneously fail to seal.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. An electrode for connection to a patient's skin to deliver electric current to the patient to stimulate the patient's heart, comprising:
    a first conductive member having a sheet-like configuration and an area resistivity of at least 0.003 ohm-cm$^2$;
    means for introducing electrical current to a centrally located portion of the first conductive member; and,
    a second conductive member having a sheet-like configuration and having one surface in contact with the first conductive member and a second surface for engaging the patient's skin, the second conductive member having an area resistivity greater than that of the first conductive member.

2. The electrode of claim 1, further comprising a conductive adhesive layer coating the second surface of the second conductive member.

3. The electrode of claim 1, further comprising an insulating layer interposed between the first and second conductive members at and surrounding the centrally located portion of the first conductive member, the area of the insulating member being substantially smaller than the areas of the first and second conductive members.

4. The electrode of claim 3, wherein the radius of the insulating layer is no greater than 20 percent of the radius of the first and second conductive members.

5. The electrode of claim 1, wherein the area resistivity of the first conductive member is at least 0.25 ohm-cm$^2$.

6. The electrode of claim 5, wherein the area resistivity of the second conductive member is at least 10 times greater than the area resistivity of the first conductive member.

7. The electrode of claim 6, wherein the area resistivity of the second conductive member is approximately 500–1,500 times greater than the area resistivity of the first conductive member.

8. The electrode of claim 7, wherein the area resistivity of the first conductive member is approximately 2.7 ohm-cm$^2$.

9. The electrode of claim 1, wherein the second conductive member comprises two layers of conductive gum adhesive and a layer of conductive rubber sandwiched therebetween, the area resistivity of the conductive rubber layer being greater than the area resistivity of each gum adhesive layer.

10. The electrode of claim 9, wherein the area resistivity of the conductive rubber layer is approximately twice as great as the area resistivity of each of the conductive gum adhesive layers.

11. The electrode of claim 9, wherein the first conductive member is circular and has a volume resistivity of approximately 35 ohm-cm and a thickness of approximately 0.76 mm, wherein the conductive rubber layer has a volume resistivity of approximately 25,000 ohm-cm and a thickness of approximately 0.51 mm, and wherein each of the conductive gum adhesive layers has a volume resistivity of 7,500 ohm-cm and a thickness of approximately 0.89 mm.

12. The electrode of claim 1, wherein the volume resistivity of the conductive rubber is at least twice as great as the volume resistivity of the conductive gum adhesive

* * * * *

UNITED STATES PATENT AND TRADEMARK OFFICE
CERTIFICATE OF CORRECTION

PATENT NO. : 4,776,350

DATED : October 11, 1988

INVENTOR(S) : Phillip A. Grossman et al.

It is certified that error appears in the above-identified patent and that said Letters Patent is hereby corrected as shown below:

| Column | Line | Error |
|--------|------|-------|
| 4 | 26 | "commerciallyavailable" should be --commercially available-- |
| 9 | 6 | "1" should be --9-- |
| 10 | 3 | add a period (--.--) after "adhesive" |

Signed and Sealed this

Twelfth Day of May, 1992

Attest:

DOUGLAS B. COMER

Attesting Officer

Acting Commissioner of Patents and Trademarks